US009889231B2

(12) United States Patent
Tsuchiya et al.

(10) Patent No.: US 9,889,231 B2
(45) Date of Patent: Feb. 13, 2018

(54) MEDICAL SUPPLIES AND METHOD OF PRODUCING THE SAME

(71) Applicant: PROSTEC Co., Ltd., Ishikawa (JP)

(72) Inventors: Hiroyuki Tsuchiya, Ishikawa (JP); Matsufumi Takaya, Chiba (JP); Masatsugu Maejima, Tokyo (JP)

(73) Assignee: PROSTEC Co., Ltd. (JP)

( * ) Notice: Subject to any disclaimer, the term of this patent is extended or adjusted under 35 U.S.C. 154(b) by 0 days.

(21) Appl. No.: 13/836,425

(22) Filed: Mar. 15, 2013

(65) Prior Publication Data

US 2013/0240365 A1    Sep. 19, 2013

Related U.S. Application Data

(62) Division of application No. 13/000,860, filed as application No. PCT/JP2009/004096 on Aug. 25, 2009.

(51) Int. Cl.
| | |
|---|---|
| *A61L 27/54* | (2006.01) |
| *A61L 27/04* | (2006.01) |
| *A61L 27/50* | (2006.01) |
| *A61L 27/56* | (2006.01) |

(52) U.S. Cl.
CPC .............. *A61L 27/54* (2013.01); *A61L 27/04* (2013.01); *A61L 27/50* (2013.01); *A61L 27/56* (2013.01); *A61L 2300/106* (2013.01); *A61L 2300/404* (2013.01); *A61L 2400/18* (2013.01)

(58) Field of Classification Search
CPC ....................................................... A61C 8/00
USPC .............. 623/16; 427/2; 604/892.1; 204/35; 433/201, 201.1, 173, 174
See application file for complete search history.

(56) References Cited

U.S. PATENT DOCUMENTS

| | | | | |
|---|---|---|---|---|
| 3,929,593 | A | * | 12/1975 | Sugiyama et al. ............. 205/105 |
| 5,478,237 | A | * | 12/1995 | Ishizawa .............. A61C 8/0012 |
| | | | | 205/318 |
| 6,740,077 | B1 | * | 5/2004 | Brandau et al. ........... 604/892.1 |
| 2005/0126918 | A1 | | 6/2005 | Kin et al. |
| 2008/0147186 | A1 | | 6/2008 | Joshi et al. |
| 2012/0111694 | A1 | | 5/2012 | Nutzel |

FOREIGN PATENT DOCUMENTS

| | | |
|---|---|---|
| CN | 1626702 | 6/2005 |
| EP | 0 037 678 A1 | 10/1981 |

(Continued)

OTHER PUBLICATIONS

Hiratsuka et al., Effect of impregnation of iodine complex on friction of anodic oxide of aluminum, 2002, Tribology Letters, vol. 13, No. 2, pp. 77-80.*

(Continued)

*Primary Examiner* — Dah-Wei D Yuan
*Assistant Examiner* — Andrew Bowman
(74) *Attorney, Agent, or Firm* — DLA Piper LLP (US)

(57) ABSTRACT

A method of producing metallic medical supplies includes supplying a metallic material as a base material; treating the base material by carrying out any one of electrochemical treatment, chemical treatment, thermal and/or mechanical treatment or a combination of two or more of these treatments to form a film having micro pores and/or micro unevennesses having a density of 5' 104/mm2 on a surface of the base material; and carrying out iodine-impregnation treatment to impregnate the film with iodine or iodine compounds.

18 Claims, 2 Drawing Sheets

(56) References Cited

FOREIGN PATENT DOCUMENTS

| JP | 2003-513001 T | 4/2003 |
|---|---|---|
| JP | 2004-515276 T | 5/2004 |
| JP | 2007-507306 T | 3/2007 |
| JP | 2008-006164 A | 1/2008 |
| RU | 2325133 | 5/2008 |
| WO | 99/53898 A1 | 10/1999 |
| WO | 02/45764 A1 | 6/2002 |
| WO | 2005/032417 A2 | 4/2005 |
| WO | 2008/056323 A1 | 5/2008 |

OTHER PUBLICATIONS

Colombian Office Action dated Nov. 7, 2013 for Colombian Application No. 12-27695-5.

Clayton N. Kraft et al., "Striated muscle microvascular response to silver implants: A comparative in vivo study with titanium and stainless steel," Journal of Biomedical Materials Research Part A, vol. 49 (1999), Issue 2, pp. 192-199.

A. Massè et al., "Prevention of Pin Track Infection in External Fixation with Silver Coated Pins: Clinical and Microbiological Results," Journal of Biochemical Materials Research Part B: Applied Biomaterials, vol. 53 (2000), Issue 5, pp. 600-604.

Hiratsuka, K., et al., "Effect of impregnation of iodine complex on friction of anodic oxide of aluminum," Tribology Letters, vol. 13, No. 2, 2002, pp. 77-80.

US Official Action dated Aug. 8, 2014 from related U.S. Appl. No. 13/000,860.

\* cited by examiner (a) DC (b) 50Hz (c) 1000Hz

MEDICAL SUPPLIES AND METHOD OF PRODUCING THE SAME

TECHNICAL FIELD

This disclosure relates to medical supplies and, particularly, to an improvement in the antimicrobial activity of medical supplies such as artificial bones and osteosynthetic and fixation devices which are implanted in living bodies prior to use.

BACKGROUND

The recent development of medical technologies has led to the situation where many technologies are used clinically for grafting implants that repair and substitute bones and joints which are defectives or have depleted functions in living bodies such as the human bodies. As to the characteristics required for each of the implants used in these technologies, the implants are desired to have the same strength as part of a living body before being substituted and also, compatibility with a living body, that is, biocompatibility. Examples of biocompatible metallic materials having such characteristics include titanium, titanium alloys, stainless steel and Co—Cr alloys. However, these metallic materials have no living activity so that they are not chemically bonded to a bone, causing problems concerning the occurrences of a gap and loosening during a long time of use.

In light of such problems, there is described in, for example, Japanese Patent Application Laid-Open No. 2008-6164, a method of forming an oxide film in which a hydrogen peroxide-containing paste is brought into contact with the surface of a metal which is a base material to thereby convert the surface of the base material into a metal oxide. According to that disclosure, an oxide film can be formed in a short time and good biocompatibility is obtained.

Further, separately from the above problems, those implants cause the problem that when the implants are grafted in living bodies, infections such as suppuration of diseased parts is caused with high incidence.

To deal with such a problem, there is the idea of using, as implant materials, Cu and Ag that are widely known to exhibit excellent antimicrobial activity. For example, C. N. Kraft, et al., Journal of Biomedical Materials Research Part A, Vol. 49 (1999), Issue 2, pages 192-199 reveals the results obtained by carrying out an experiment in which Ag known to exhibit high antimicrobial activity is transplanted as an implant (made of pure silver) to an animal (hamster). According to these results, it is necessary to cautiously decide whether to use Ag as an implant material because a silver implant causes severer inflammation and swelling as compared with a titanium or stainless steel implant, showing that the silver implant is deteriorated in affinity to a living body.

Further, A. Masse, et al., Journal of Biochemical Materials Research Part B: Applied Biomaterials, Vol. 53 (2000), Issue 5, pages 600-604 reports the result of an experiment concerning inhibition to pin-infections in the case of using an external fixation pin coated with Ag. According to those results, it is not observed that bacterial cells are sufficiently reduced by the Ag coating and it is observed that a rise in Ag level in blood by the grafting of the Ag-coated external fixation pin in a living body.

It could therefore be helpful to provide medical supplies which can inhibit infections with various bacteria for a long period of time, have excellent antimicrobial activity, and are superior in the durability of antimicrobial activity and also superior in biocompatibility, and to provide a method of producing the medical supplies.

SUMMARY

We thus provide:
(1) Metallic medical supplies using a metal material as a base material, the medical supplies including a film having micro pores and/or micro unevennesses on the surface of the base material, wherein the micro pores and/or micro unevennesses are impregnated with iodine or iodine compounds.
(2) The metallic medical supplies according to (1), wherein the film includes the micro pores and/or micro unevennesses having a density of at least $5 \times 10^4/\text{mm}^2$ or more.
(3) The metallic medical supplies according to (1) or (2), wherein the film is formed by any one of electrochemical treatment, chemical treatment, thermal and/or mechanical treatment or a combination of two or more of these treatments.
(4) The metallic medical supplies according to (3), wherein the electrochemical treatment is anodic oxidation treatment, the chemical treatment is medicine treatment, the thermal and/or mechanical treatment is any one of heating treatment, thermal processing treatment and mechanical processing treatment.
(5) The metallic medical supplies according to any one of (1) to (4), wherein the iodine compound is polyvinyl pyrrolidone iodine, β-cyclodextrin iodine or silver iodide.
(6) The metallic medical supplies according to any one of (1) to (5), wherein the metallic material is a pure metal selected from the group consisting of Ti and Co or an alloy selected from the group consisting of a Ti alloy, a Co alloy, stainless steel and a Co—Cr alloy.
(7) Metallic medical supplies using a metal material as a base material, the medical supplies including a film subjected to anodic oxidation treatment having micro pores having a density of at least $5 \times 10^4/\text{mm}^2$ on the surface of the base material, wherein the micro pores are impregnated with iodine or iodine compounds.
(8) The metallic medical supplies according to (7), wherein the iodine compound is polyvinyl pyrrolidone iodine, β-cyclodextrin iodine or silver iodide.
(9) The metallic medical supplies according to (7) or (8), wherein the film has a thickness of 3 μm or more.
(10) The metallic medical supplies according to any one of (7) to (9), wherein the base material is made of any one of Ti or Ti alloy, stainless steel, and a Co—Cr alloy.
(11) A method of producing metallic medical supplies, the method including using a metallic material as a base material, treating the base material by carrying out any one of electrochemical treatment, chemical treatment, thermal and/or mechanical treatment or a combination of two or more of these treatments to form a film having micro pores and/or micro unevennesses having a density of $5 \times 10^4/\text{mm}^2$ on the surface of the base material, and carrying out iodine-impregnation treatment to impregnate the film with iodine or iodine compounds, to make medical supplies.
(12) The method of producing metallic medical supplies according to (11), wherein the electrochemical treatment is anodic oxidation treatment, the chemical treatment is medicine treatment, the thermal and/or mechanical treatment is any one of heating treatment, thermal processing treatment and mechanical processing treatment.

(13) The method of producing metallic medical supplies according to (12), wherein the anodic oxidation treatment is a treatment in which an acid electrolytic bath or an alkali electrolytic bath is used as an electrolytic solution, and pulsed current having a frequency of 50 to 10000 Hz is applied to the base material in the electrolytic solution to carry out electrolysis treatment.

(14) The method of producing metallic medical supplies according to (12), wherein the medicine treatment is a treatment in which an alkali bath or acid bath having a liquid temperature of 30° C. or more is used and the base material is dipped in the alkali bath or acid bath.

(15) The method of producing metallic medical supplies according to (12), wherein the mechanical processing treatment is a shot blasting.

(16) The method of producing metallic medical supplies according to any one of (11) to (15), wherein the iodine compound is polyvinyl pyrrolidone iodine, β-cyclodextrin iodine or silver iodide.

(17) The method of producing metallic medical supplies according to any one of (11) to (16), wherein the base material is made of any one of Ti or Ti alloy, stainless steel, and a Co—Cr alloy.

DETAILED DESCRIPTION

Figure 1:
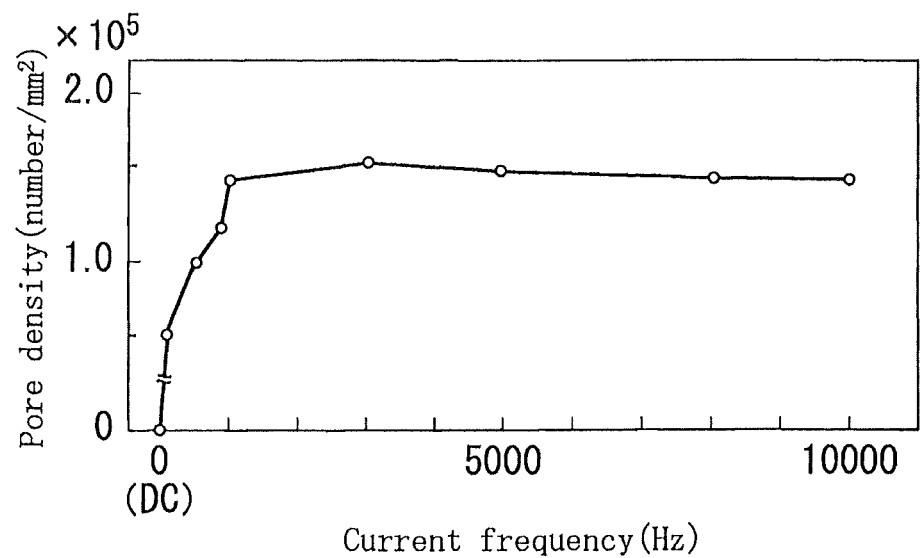
FIG. 1 is a graph showing the relation between the pore density of a film formed in anodic oxidation treatment and the frequency of pulse current load.

We focused our attention on iodine and iodine compounds as materials having antimicrobial activity. Iodine has sterilizing activity and antimicrobial activity, and is also used as disinfectants and is said to have little toxicity to living bodies. We thus impregnated the surface of an implant base material with iodine or iodine compounds to inhibit infections associated with an implant. We found that if the surface of an implant base material is impregnated with iodine or iodine compounds and iodine is allowed to be discharged gradually, this enables the implant itself to be sterilized and is also very effective to maintain the antimicrobial activity afterward. We also found that, when the base material was anodically oxidized in an electrolytic solution having a specific composition by using pulsed current having a frequency in a predetermined range, an oxide film having many micro pores was formed on the base material and, also, these micro pores could be impregnated with iodine or iodine compounds, showing that these pores were very effective to improve the continuation of antimicrobial activity.

First, a fundamental experiment will be described.

A Ti alloy (mass % basis, 6% Al-4% V-rest Ti; JIS type-60 alloy) was used as the base material to produce disc-like test piece (plate thickness: 1.5 mm). These test pieces were subjected to degreasing treatment and then to anodic oxidation treatment. In the anodic oxidation treatment, the test piece was electrolyzed at a constant voltage (150 V) for 5 minutes in an acid electrolytic solution (solution temperature: room temperature) of a mixture bath containing sulfuric acid (35 g/l)-phosphoric acid (25 g/l)-aqueous hydrogen peroxide (10 g/l). In this case, though the current load was made to have an initial current density of 8 A/dm$^2$, the current value was dropped along with passage of time because of the electrolysis at constant voltage. 50 to 10000 Hz pulsed current was used. The test was also made by using direct current (DC) as the current load.

The anodically oxidized test piece was cleaned with water and then subjected to iodine-impregnation treatment in which the test piece was dipped in an aqueous iodine compound solution prepared by dissolving 0.5 mass % of a polyvinyl pyrrolidone iodine (PVPI) which was an iodine compound in pure water. The test piece was arranged on the anode side and a pure Ti plate was arranged on the cathode side, and the test piece was electrolyzed at a constant voltage of 120 V for 5 minutes to cause electrophoresis, thereby impregnating an oxide film of the surface of the test piece with the iodine compound. In this impregnation with iodine compound, the initial current density was set to about 0.2 A/dm$^2$. A part of the test pieces were not subjected to the impregnation with iodine compound.

First, the anodically oxidized test pieces were subjected to a scanning electron microscope (magnification: 2500 times) to be used to observe the surface structure of the oxide film formed on the surface of the test piece. Each test piece was observed from five or more visual fields to measure the number of pores formed in the oxide film in each visual field. Then, an arithmetic average of the obtained values was calculated to determine the number of pores of the oxide film formed on the surface of each test piece. In this case, the section of each test piece was also observed by a scanning electron microscope (magnification: 2500 times) to measure the thickness of the formed oxide film.

Further, with regard to the test pieces subjected to anodic oxidation treatment and the test pieces subjected to anodic oxidation treatment and iodine-impregnation treatment, an antimicrobial activity test was made by the film covering method according to the provisions of JIS Z 2801. *Escherichia coli* (JCM 1649 strains) was used as the pathogenic organ and the cells number left after a prescribed time (24 h) passed was measured to evaluate the antimicrobial activity of the test piece. The test was repeated two times each. When the cell numbers left after a prescribed time passed is smaller, the test piece is evaluated to be superior in antimicrobial activity. When the cell numbers which were, at first, 36000/ml (3.6×10$^4$/ml) decreased to less than 10/ml after a prescribed time (24 h) passed, this was rated as 4 (antimicrobial activity value), when the cell numbers were 10 or more and less than 100/ml, this was rated as 3 (antimicrobial activity value), when the cell numbers were 100 or more and less than 1000/ml, this was rated as 2 (antimicrobial activity value), when the cell numbers were 1000 or more and less than 10000/ml, this was rated as 1 (antimicrobial activity value), and when the cell numbers were 10000 or more, this was rated as 0 (antimicrobial activity value).

The obtained results are shown in Table 1.

TABLE 1

| Test piece No. | Base material* | Anodic oxidation treatment | | Iodine-impregnation treatment | Antimicrobial activity rating |
| --- | --- | --- | --- | --- | --- |
| | | Current load | | | |
| | | Type ** | Frequency Hz | Treated or untreated | After passed 24 hr |
| 1 | A | b | — | Untreated | 0 |
| 2 | A | b | — | Treated | 1 |
| 3 | A | a | 50 | Untreated | 0 |
| 4 | A | a | 50 | Treated | 2 |
| 5 | A | a | 500 | Untreated | 0 |

TABLE 1-continued

| Test piece No. | Base material* | Anodic oxidation treatment | | Iodine-impregnation treatment | Antimicrobial activity rating |
| --- | --- | --- | --- | --- | --- |
| | | Current load | | | |
| | | Type ** | Frequency Hz | Treated or untreated | After passed 24 hr |
| 6 | A | a | 500 | Treated | 2 |
| 7 | A | a | 800 | Untreated | 0 |
| 8 | A | a | 800 | Treated | 3 |
| 9 | A | a | 1000 | Untreated | 0 |
| 10 | A | a | 1000 | Treated | 4 |
| 11 | A | a | 3000 | Untreated | 0 |
| 12 | A | a | 3000 | Treated | 4 |
| 13 | A | a | 5000 | Untreated | 0 |
| 14 | A | a | 5000 | Treated | 4 |
| 15 | A | a | 8000 | Untreated | 0 |
| 16 | A | a | 8000 | Treated | 3 |
| 17 | A | a | 10000 | Untreated | 0 |
| 18 | A | a | 10000 | Treated | 3 |

*A: Ti alloy (JIS type-60 alloy)
** a: pulsed current, b: direct current

In the case where the iodine-impregnation treatment is not carried out, but only anodic oxidation treatment is carried out, the antimicrobial activity value is 0 and no improvement in antimicrobial activity is observed.

The antimicrobial activity is improved more significantly in the case of performing anodic oxidation treatment by adding pulsed current at a frequency of 50 Hz or more than in the case of performing anodic oxidation treatment by adding direct current. It is clarified that the antimicrobial activity is significantly improved when anodic oxidation treatment is performed by applying pulsed current at a frequency of, particularly, 800 Hz or more and more preferably 1000 to 5000 Hz. This is clarified from the relation between the density of the formed micro pores and the frequency of the pulsed current load in the anodic oxidation treatment as illustrated in FIG. 1.

Figure 3:
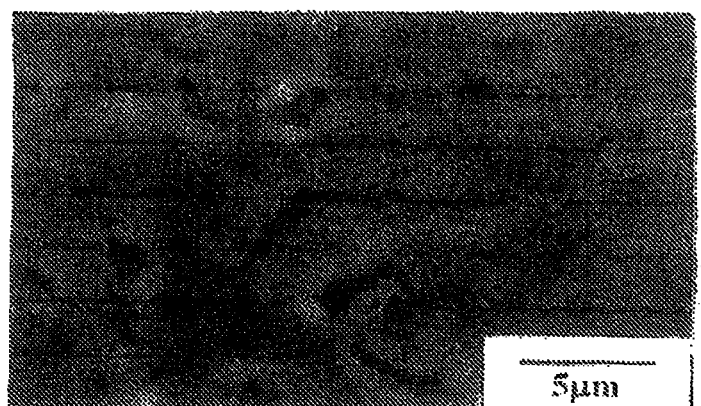
FIG. 3 is a scanning electron micrograph showing the surface state of a film formed by anodic oxidation treatment.
Figure 3:
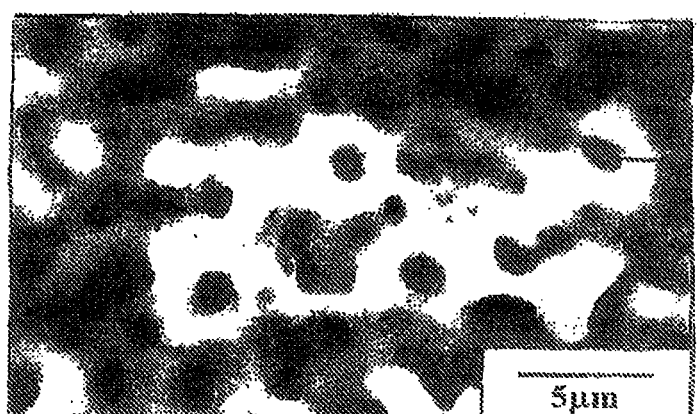
Figure 3:
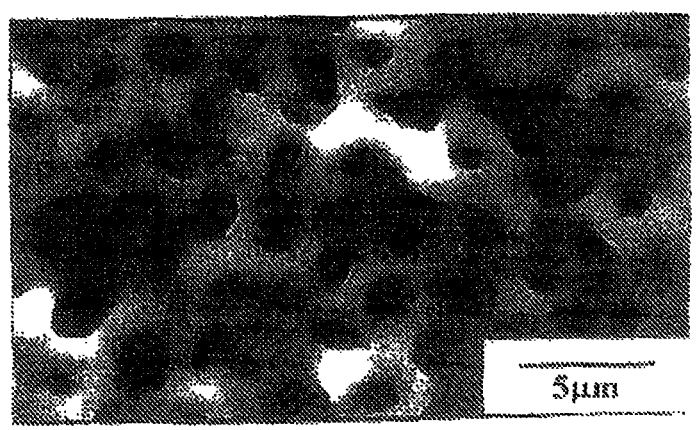

It is found from FIG. 1 that when the frequency of the pulsed current load is 50 Hz or more, the density of micro pores to be formed is significantly increased to as high as $5 \times 10^4/mm^2$. When the frequency is 0, that is, when direct current is applied, only groovy unevenness is formed on the film and almost no micro pore is formed as shown in FIG. 3(a). When the frequency of the applied pulse current is 50 Hz on the contrary, the groovy unevenness disappears and many micro pores are clearly formed on the film as shown in FIG. 3(b). Moreover, when the frequency of the applied pulse current is as high as 1000 Hz, many more micro pores are formed as shown in FIG. 3(c). We found from the comparison shown in Table 1 and FIG. 1 that the supplies which have a film having micro pores increased in pore density to at least $5 \times 10^4/mm^2$ or more and which has been subjected to iodine-impregnation treatment are able to have excellent antimicrobial activity.

Figure 2:
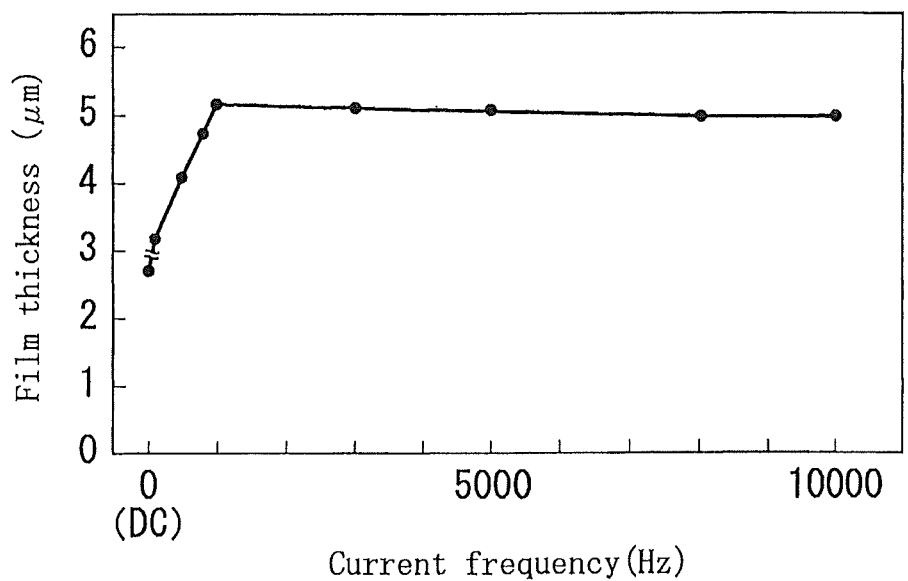
FIG. 2 is a graph showing the relation between the thickness of a film formed in anodic oxidation treatment and the frequency of pulse current load.

Further, as shown in FIG. 2, we found that, if pulse current having a frequency of 50 Hz or more is applied to carry out anodic oxidation treatment, many micro pores are formed and a film 3 μm or more in thickness can be formed.

We found from the above results that when pulse current having a frequency of 50 Hz or more is applied to carry out anodic oxidation treatment, a film which contains many micro pores described above and has a thickness of, preferably 3 μm or more can be formed on the base material and that when the film is impregnated with iodine or iodine compounds, the antimicrobial activity of the base material is significantly improved.

Medical supplies which have excellent antimicrobial activity and are superior in the durability of antimicrobial activity and also in biocompatibility can be produced easily at low costs, producing an outstanding industrial effect. Further, when the medical supplies are used as, for example, an implant to be grafted in a living body, such an effect is obtained that infections which are large problems when usual medical supplies are grafted in a living body can be inhibited for a long period of time.

We thus provide medical supplies using a base material made of a metallic material, and provided with a film having micro pores and/or micro unevennesses on the base material. The term "micro pores and/or micro unevennesses" used herein means the surface state of the base material changed from the initial state by artificially carrying out heat treatment, mechanical treatment, electrochemical treatment or chemical treatment or combinations of these treatments. Then, the term "micro pore" means a circular or polygonal pore having an area-equivalent circle diameter of about 1 to 10 μm. Further, the term "micro unevennesses" means the surface state on which unevennesses having a depth of several micrometers (μm) to several hundreds of micrometers (surface roughness Ra: about several micrometers (μm) to several hundreds of micrometers (μm)) exist as these pores are deformed or integrated.

The film to be formed on the surface of the base material may be one only having micro pores and/or micro unevennesses such as those mentioned above and no particular limitation is imposed on a method of forming the film. However, the film is preferably one formed by any one of electrochemical treatment, chemical treatment, thermal and/or mechanical treatment or a combination of two or more of these treatments. It is preferable to adopt anodic oxidation treatment as the electrochemical treatment, medicine treatment as the chemical treatment, heating treatment as the thermal treatment, thermal processing treatment as the thermal and mechanical treatment, and mechanical processing treatment as the mechanical treatment. These treatments enable easy formation of a film having micro pores and/or micro unevennesses having a desired density. The desired density of the micro pores and/or micro unevennesses is preferably at least $5 \times 10^4/mm^2$ or more. When such a film having micro pores and/or micro unevennesses having a desired density is formed on the surface of the base material, the surface of the base material can be impregnated stably and sufficiently with iodine or iodine compounds which improve the antimicrobial activity and sterilizing activity of the supplies.

Then, micro pores or micro unevennesses of the film are impregnated with iodine or iodine compounds. Since iodine has antimicrobial activity and sterilizing activity, the antimicrobial activity and sterilizing activity of the supplies are improved by the action of iodine which is gradually released from iodine or iodine compound with which the micro pores or micro unevennesses of the film are impregnated. When, particularly, micro pores or micro unevennesses of the film are impregnated with iodine or iodine compounds, this has the benefit that the area of the surface capable of holding iodine or iodine compounds is more increased than in the case of applying iodine or iodine compound to a plane, enabling the above iodine or iodine compound to be supported in a large amount and also, the release of iodine from iodine or iodine compounds is continued gradually for a long time. This makes it possible to maintain the antimicrobial activity and sterilizing activity of the supplies for a long period of time.

Examples of the iodine compound with which the supplies are impregnated may include:
- inorganic compounds such as silver iodide, potassium iodide, nickel iodide, iron iodide and tin iodide;
- organic compounds, for example, chain saturated hydrocarbons and their derivatives such as methyl iodide, ethyl iodide, propyl iodide, butyl iodide, and isopropyl iodide;
- also, chain unsaturated hydrocarbons and their derivatives such as vinyl iodide, anyl iodide, crotyl iodide, propargyl iodide, and phenylacetylene iodide;
- also, aromatic hydrocarbons and their derivatives such as iodobenzene, benzyl iodide, benzoyl iodide, phenacyl iodide, xylylene iodide, phthalein iodide, hydroquinone iodide, and cyclodextrin-iodine inclusion compounds;
- also, hetero-compounds such as trimethylsulfonium iodide and triphenyl-sulfonium iodide; and
- hetero-compound polymers such as polyvinyl pyrrolidone iodine and polyvinyl-phthalimide iodine.

Among the above iodine compounds, hetero-compound polymers such as polyvinyl pyrrolidone iodine, aromatic hydrocarbons and their derivatives such as β-cyclodextrin iodine or inorganic compounds such as silver iodide are preferable as the iodine compound with which the supplies are impregnated, from the viewpoint of safety to the human body, environmental integrity and biocompatibility.

Though no particular limitation is imposed on the type of metallic material to be used as the base material insofar as the metallic material is suitable for use as medical supplies, Ti or Co is preferably used if it is a pure metal or a Ti alloy, Co alloy, stainless steel or Co—Cr alloy is preferably used if it is an alloy. It is more preferable to use Ti and Ti alloy, stainless steel or Co—Cr alloy taking it into account to transplant the supplies to living bodies. Ti is preferably pure Ti prescribed as JIS type-1 or JIS type-2 or a Ti alloy prescribed as JIS type-60 (6% Al-4% V—Ti alloy), JIS type-61 (3% Al-2% V—Ti alloy), 15-3-3 alloy, JIS type-11 or JIS type-12 are each applicable. Further, as the above stainless steel, austenite stainless steels such as SUS 302, SUS 304, SUS 316, SUS 316L, SUS 317J4L, SUS 329J1 and SUS 329J3L are preferable from the viewpoint of non-magnetism. Further, as the above Co—Cr alloy, a stellite 20 alloy having a composition of 63.0% Cr-6.0% Mo-2.0% Ni-0.25% C-rest Cr is preferable from the viewpoint of strength and corrosion resistance.

Next, a method of producing medical supplies will be described.

A base material made of any one of the metallic materials is preferably formed into a predetermined shape and then subjected to degreasing treatment. Then, the base material is subjected to any one of electrochemical treatment, chemical treatment, thermal and/or mechanical treatment or a combination of two or more of these treatments to form a film on the surface of the base material. It is preferable to adopt anodic oxidation treatment as the electrochemical treatment, medicine treatment as the chemical treatment, heating treatment as the thermal treatment, thermal processing treatment as the thermal and mechanical treatment and mechanical processing treatment as the mechanical treatment. The method will be described concerning the case of performing anodic oxidation treatment to form a film on the surface of the base material as an example. It is needless to say that the method is not limited to the anodic oxidation treatment.

In the anodic oxidation treatment, the base material formed into a predetermined shape is dipped in an electrolytic solution and used as the anode to apply current to electrolyze. As the electrolytic solution to be used, an acid electrolytic bath or alkali electrolytic bath is used corresponding to the type of base material.

Examples of the acid electrolytic bath may include a sulfuric acid-water mixture bath (for example, content of sulfuric acid: 5 to 30 mass % and preferably 10 to 25 mass %), sulfuric acid-phosphoric acid-water mixture bath (for example, sulfuric acid 35 g/l and phosphoric acid 25 g/l), sulfuric acid-phosphoric acid-aqueous hydrogen peroxide-water mixture bath (for example, sulfuric acid 35 g/l, phosphoric acid 25 g/l, and aqueous hydrogen peroxide 10 g/l), sulfuric acid-phosphoric acid-ascorbic acid-water mixture bath (for example, sulfuric acid 35 g/l, phosphoric acid 25 g/l and ascorbic acid 10 g/l) and hydrochloric acid-aqueous hydrogen peroxide-formalin-water mixture bath (for example, hydrochloric acid 40 mass %, aqueous hydrogen peroxide 2 mass % and formalin 10 mass %).

Further, examples of the alkali electrolytic bath may include potassium hydroxide-potassium fluoride-sodium phosphate-aluminum hydroxide-water mixture bath (for example, potassium hydroxide 165 g/l, potassium fluoride 35 g/l, sodium phosphate 35 g/l and aluminum hydroxide 35 g/l).

It is preferable to use the acid electrolytic bath when the base material is Ti or a Ti alloy or stainless steel, and the alkali electrolytic bath when the base material is a Co—Cr alloy.

In the electrolysis, pulsed current having a frequency of 50 Hz or more and preferably 10000 Hz or less is used as the current load. When pulsed current having a frequency of 50 Hz or more is used as the current load, a film including micro pores and/or micro unevennesses having a density of at least $5 \times 10^4 / mm^2$ can be formed. When the current load is direct current (DC), only a film containing neither micro pore nor micro-unevenness can be formed as shown in FIG. 3(a). Such a film can be insufficiently impregnated with iodine and an iodine compound with result that sufficient antimicrobial activity cannot be imparted to the supplies. In this case, large-scaled equipment is required to generate pulsed current having a frequency exceeding 10000 Hz and, therefore, the cost required for the equipment is increased, bringing about high production cost. From the above reason, the current applied in the anodic oxidation treatment is preferably 50 to 10000 Hz pulsed current. The frequency is more preferably 1000 to 5000 Hz from the viewpoint of the number of micro-pores to be formed.

Medicine treatment as the chemical treatment, heating treatment as the thermal treatment, heating processing treatment as the thermal and mechanical treatment, or mechanical processing treatment as the mechanical treatment or a combination of two or more of these treatments may be adopted in place of the anodic oxidation treatment as the electrochemical treatment.

Examples of the medicine treatment may include a method in which a high-temperature alkali-type bath or an acid bath is used and the base material is dipped in this bath to form chemically treated film having micro pores and/or micro unevennesses on the surface of the base material. A method in which as the high-temperature alkali-type bath, for example, a 140° C. sodium hydroxide-potassium nitrate-water mixture bath (for example, 60 parts by weight of sodium hydroxide, 40 parts by weight of potassium nitrate and 500 parts by weight of water) is used and the base material is dipped in this bath for 10 minutes and a method in which as the acid bath, for example, a 30° C. oxalic acid-hydrogen peroxide-water mixture bath (for example, 25 mass % of oxalic acid (100 g/l) and 3.5 mass % of hydrogen peroxide (30%)) is used and the base material is dipped in this bath for 30 minutes are exemplified. This treatment is preferably applied in the case of using stainless steel such as SUS 304 as the base material.

Further, examples of the heating treatment may include a method in which the base material is heated (heating temperature: 600 to 800° C. and preferably 700° C.×1 hr) in the atmosphere to form a film (oxide film) on the surface of the base material. Further, examples of the thermal processing treatment may include methods in which the surface of the base material is irradiated with an electron beam or laser beam. Further, examples of the mechanical processing treatment may include methods using a shot blasting. In these treatments, it is essential to make an examination in advance before determining the treatment conditions so that a film having micro unevennesses or micro pores having a desired surface structure. In this case, these treatments are preferably applied when stainless steel or a Co—Cr alloy is used as the base material.

Treatment such as anodic oxidation treatment is performed to form a film having micro pores or micro unevennesses on the surface of the base material and then, iodine-impregnation treatment is carried out to impregnate the film with iodine or iodine compounds.

The iodine-impregnation treatment can be carried out as follows: the base material which has been subjected to, for example, anodic oxidation treatment is cleaned with water, then dipped in an aqueous iodine or iodine compound solution and direct current is applied by using the base material as the anode to carry out electrolysis at a constant voltage or constant current density. The aqueous solution used for the electrolysis is preferably an aqueous solution containing 0.1 to 1.0 mass % of iodine or iodine compounds. When the amount of iodine or iodine compounds is less than 0.1 mass %, the content of iodine with which the film is impregnated is so small that desired antimicrobial activity cannot be developed. Even if iodine or iodine compound is added in an amount exceeding 1.0 mass % on the other hand, the effect is saturated and this is economically disadvantageous. The amount of iodine or iodine compound is more preferably 0.3 to 0.5 mass %.

Further, as the iodine compound to be added in the aqueous solution, the iodine compounds are all preferable. Among these compounds, polyvinyl pyrrolidone iodine (PVPI), β-cyclodextrin iodine (BCDI) and silver iodide are preferable from the viewpoint of biocompatibility.

In the iodine-impregnation treatment, the constant voltage anodizing is preferably carried out at a constant voltage ranging from 100 to 200 V for 1 to 10 minutes. The constant current density anodizing is preferably carried out at a constant current density ranging from 0.05 to 10 A/dm$^2$ for 1 to 10 minutes.

Our medical supplies and methods will be described in more detail by way of Examples.

EXAMPLES

Example 1

A Ti alloy (mass % basis, 6% Al-4% V-rest Ti; JIS type-60 alloy) and stainless steel (SUS 304) were used as base materials to manufacture discs (plate thickness: 2.0 mm) as test pieces for in vitro test and external fixation pins for a rabbit as test pieces for in vivo test.

Among these test pieces, the Ti alloy test pieces were subjected to degreasing treatment and then to anodic oxidation treatment. In the anodic oxidation treatment, the test piece was electrolyzed at a constant voltage (150 V) for 5 minutes in an acid electrolytic solution (solution temperature: ambient temperature) of a mixture bath containing sulfuric acid (35 g/l)-phosphoric acid (25 g/l)-aqueous hydrogen peroxide (10 g/l). In this case, though the current load was at an initial current density of 8 A/dm$^2$, the current value was dropped along with passage of time because of the electrolysis at constant voltage. In this case, pulsed current having a frequency of 10000 Hz was used. The test pieces which the anodic oxidation treatment was not performed was regarded as comparative examples.

First, the anodically oxidized test pieces (Ti alloy test pieces) were subjected to a scanning electron microscope (magnification: 2500 times) to observe the surface structure of the oxide film formed on one surface of each test piece in five or more visual fields, thereby measuring the number of pores formed in the oxide film in each visual field. Then, an arithmetic average of the values obtained in the visual fields was calculated to determine the number of pores of the oxide film formed on the surface of each test piece. Further, the section of each test piece was observed by a scanning electron microscope (magnification: 2500 times) in five visual fields to measure an average thickness of the oxide film formed on the surface.

Then, the anodically oxidized test pieces (Ti alloy test pieces) were cleaned with water for one minute. After cleaning with water, the test piece was dipped in an aqueous iodine compound solution prepared by dissolving 0.5 mass % of polyvinyl pyrrolidone iodine (PVPI) which was an iodine compound in pure water and the test piece was settled on the anode side and a pure Ti plate was settled on the cathode side to perform electrolysis at a constant voltage of 120 V, thereby carrying out iodine-impregnation treatment. In the iodine-impregnation treatment, the initial current density was set to about 0.2 A/dm$^2$ to cause electrophoresis to impregnate the oxide film formed on the surface of the test piece with the iodine compound.

In this case, the test pieces which were not anodically oxidized were degreased and cleaned with water for one minute prior to the test.

Then, using a part of these treated obtained test pieces (discs), an antimicrobial activity test was made for in vivo test according to the provisions of JIS Z 2801. As the pathogenic organ, *Staphylococcus aureus* (ATCC 25923) and *Escherichia coli* (MG 1455) were used. The test was repeated 15 times for each test piece. As the cells number left after a predetermined time passed is smaller, the test piece is evaluated to be superior in antimicrobial activity.

Further, using the obtained test piece (semicircular plate), the cytotoxicity of the test piece was evaluated for in vitro test by the colony forming method using rat fibroblast cell line V79. The test piece was dipped in a culture fluid contained in a Petri dish and the above V79 was inoculated on the test piece to confirm the formation of colonies for the evaluation.

Further, using the obtained rabbit external fixation pin, 6 Japan white house rabbits were used and the pin pierced through each of the thighbones for an in vivo test. After 14 days, the rabbit was put to a gentle and easy death to make histological analysis and the degrees of the inflammation and infection of the tissue around the pin-pierced part were observed to give percentile scores to these degrees to evaluate. The evaluation items are as follows: inflammation of the pin-pierced part, abscess around the pin, marrow, and inflammation around the tip of the pin. The point was 2 when the inflammation or formation of abscess caused by the pin was serious illness, 1 when the inflammation or formation of abscess was minor, 2 when marrow formed abscess and 1 when the marrow was minor and 0 in other cases, to evaluate by the total points of the evaluation items. As the total point of the evaluation items is smaller, inflammation and infection are regarded as small. Further, at the same time, osteoid formation on the surface of the pin was confirmed to evaluate osteoconductivity.

The results obtained are shown in Table 2.

Moreover, we confirmed that our Example is similar to the Comparative Examples in that the colonies of rat fibroblast cell line V79 are well formed, so that it has no cytotoxicity.

Example 2

Stainless steel (SUS 304) was used as a base material to manufacture disc-like test pieces (plate thickness: 2 mm) for an antimicrobial test. These test pieces were each washed with an acid and then subjected to anodic oxidation treatment or to medicine treatment. In the acid washing treatment, the test pieces were dipped in an aqueous mixture solution of nitric acid (5%)-hydrofluoric acid (3%) at a liquid temperature of 40° C. for 3 minutes. In the anodic oxidation treatment, the test pieces were electrolyzed at a

TABLE 2

| Test piece No. | Base material* | Anodic oxidation treatment | Current load Type** | Current load Frequency Hz | Structure of an oxide film Number of micro pores (number/mm²) | Structure of an oxide film Film thickness µm | Antimicrobial activity Cells number after holding for 24 hr*** *Staphylococcus aureus* | Antimicrobial activity Cells number after holding for 24 hr*** *Escherichia coli* | Cytotoxicity V79 CELL Colony formability | Histological evaluation Total score of infamemation and infection | Histological evaluation Osteoconductivity | Remarks |
|---|---|---|---|---|---|---|---|---|---|---|---|---|
| A1 | A | Treated | a | 1000 | 1.5 × 10⁵ | 5.2 | 0.07 | 0 | Good | 2.92 | ○○ | Example of the present invention |
| A2 | A | Untreated | — | — | — | — | 181 | 1281 | Good | 4.42 | ○ | Comparative Example |
| A3 | B | Untreated | — | — | — | — | 347 | 1600 | Good | 4.92 | △ | Comparative Example |

*A: Ti alloy (JIS type-60), B: stainless steel (SUS304)
**a: pulsed
***Initial number of bacteria: about 2000

We found that an oxide film having micro pores as many as $5\times10^4/\text{mm}^2$ or more in number is formed in an Example (test piece No. A1).

Further, in that Example (test piece No. A1), the formation of colonies is significantly suppressed, so that the number of *Staphylococcus aureus* which is about 2000 before the start of the antimicrobial test is reduced to an average of 0.07 after 24 hr and also, the number of *Escherichia coli* which is about 2000 before the start of the antimicrobial test is reduced to an average of 0 after 24 hr, showing that the Example is superior in antimicrobial activity. In the Comparative Examples, on the other hand, the cells number observed after 24 hr is 181 (test piece No. A2) and 347 (test piece No. A3) in the case of *Staphylococcus aureus* and 1281 (test piece No. A2) and 1600 (test piece No. A3) in the case of *Escherichia coli*. These differences are statistically significant.

Further, in the Example, the total point of the evaluation of inflammation and infection is significantly lower than in the Comparative Examples and, therefore, the Example reduces inflammation and infection. Further, this difference from the Comparative Examples is also statistically significant and this shows that our Example reduces infection induced by a pin and is superior in antimicrobial activity and biocompatibility. Further, our Example is similar to titanium in good osteoid and bone formation and it may be said that our Example has sufficient osteoconductivity.

constant voltage (100 V) for 15 minutes by using the test piece as the anode and pure Ti plate as the cathode in an acid electrolytic solution (solution temperature: ambient temperature) of a mixture bath containing hydrochloric acid (47 mass %)-aqueous hydrogen peroxide (2 mass %)-formalin (10 mass %)-water. As the current load, pulsed current having a frequency of 3000 Hz was used. The initial current value was 3.5 A/dm². In the medicine treatment, the test pieces were dipped in a 30° C. mixture bath of oxalic acid (25 mass %)-hydrogen peroxide (3.5 mass %)-distilled water which was a high-temperature acid bath for 30 minutes.

The test pieces which were anodically oxidized or treated using a medicine were subjected to a scanning electron microscope (magnification: 2500 times) to observe the surface structure of the film (oxide film) formed on the surface of each test piece in five or more visual fields, thereby measuring the number of pores formed in the film in each visual field. Then, an arithmetic average of the values obtained in the visual fields was calculated to determine the number of pores of the film formed on the surface of each test piece. Further, the section of each test piece was observed by a scanning electron microscope (magnification: 2500 times) in five visual fields to measure an average thickness of the film formed on the surface.

Then, a part of each of the test pieces was cleaned with water. After cleaning with water, the test piece was dipped in an aqueous iodine compound solution prepared by dissolving 0.5 mass % of polyvinyl pyrrolidone iodine (PVPI)

which was an iodine compound in pure water and the test piece was settled on the anode side and a pure Ti plate was settled on the cathode side to perform electrolysis at a constant voltage of 120 V (direct current (DC)) for 5 minutes to cause electrophoresis, thereby carrying out iodine-impregnation treatment to impregnate the oxide film formed on the surface of the test piece with the iodine compound. In the iodine-impregnation treatment, the initial current density shown was about 0.2 A/dm².

With regard to the test pieces which were only anodically oxidized or treated using a medicine and test pieces subjected to iodine-impregnation treatment after anodically oxidized or treated using a medicine, an antimicrobial activity test was made by the film covering method according to the provisions of JIS Z 2801. As the pathogenic organ, Escherichia coli (JCM 1649 strain) was used and cell numbers left after a predetermined time (24 h) passed was measured to evaluate the antimicrobial activity. As the cell numbers left after a predetermined time passed decreases, the test piece is evaluated to be superior in antimicrobial activity. When cell numbers which were 42000/ml (4.2×10⁴/ml) at first were measured after a predetermined time (24 h) passed, the case where the cell numbers were reduced to less than 10/ml was rated as 4 (antimicrobial activity value), the case where the cell numbers were reduced to 10/ml or more and less than 100/ml was rated as 3 (antimicrobial activity value), the case where the cell numbers were reduced to 100/ml or more and less than 1000/ml was rated as 2 (antimicrobial activity value), the case where the cell numbers were reduced to 1000/ml or more and less than 10000/ml was rated as 1 (antimicrobial activity value), and the case where the cell numbers were 10000/ml or more was rated as 0 (antimicrobial activity value).

The results obtained are shown in Table 3.

facture disc-like test pieces (plate thickness: 5.0 mm) for an antimicrobial test. These test pieces were each washed with an acid and then subjected to anodic oxidation treatment.

In the anodic oxidation treatment, the test piece was electrolyzed at a constant voltage (150 V, direct current (DC)) for 15 minutes by using the test piece as the anode and pure Ti plate as the cathode in an alkali electrolytic solution (solution temperature: room temperature) of a mixture bath containing potassium hydroxide (165 g/l)-potassium fluoride (35 g/l)-sodium phosphate (35 g/l)-aluminum hydroxide (35 g/l)-water. As the current load, pulsed current having a frequency of 5000 Hz was used. The initial current value was 8 A/dm².

The obtained test pieces were subjected to a scanning electron microscope (magnification: 2500 times) to observe the surface structure of the film (oxide film) formed on the surface of each test piece, thereby determining the number of pores formed on the surface of each test piece and the average thickness of the film in the same manner as in Example 2.

Then, a part of the test pieces subjected to these treatments were cleaned with water. Then, the test piece was dipped in an aqueous iodine compound solution prepared by dissolving 0.5 mass % of polyvinyl pyrrolidone iodine (PVPI) which was an iodine compound in pure water and the test piece was settled on the anode side and a pure Ti plate was settled on the cathode side to perform electrolysis at a constant voltage of 150 V (direct current (DC)) for 5 minutes to cause electrophoresis, thereby carrying out iodine-impregnation treatment to impregnate the oxide film formed on

TABLE 3

| Test piece No. | Base material* | Anodic oxidation treatment Current load Type** | Anodic oxidation treatment Current load Frequency Hz | Medicine treatment | Film Presence or absence of micro pores or micro unevenesses | Film Number of micro pores (number/mm²) | Film Film thickness (μm) | Iodine-impregnation treatment Treated or untreated | Evaluation of antimicrobial activity Cells number after holding for 24 hr | Remarks |
|---|---|---|---|---|---|---|---|---|---|---|
| 21 | B | A | 3000 | — | Present | 16 × 10⁴ | 4.9 | Untreated | 0 | Comparative Example |
| 22 | | | | | | | | Treated | 4 | Example of the present invention |
| 23 | B | — | — | High-temperature mixture solution*** | Present | 8.6 × 10⁴ | 1.2 | Untreated | 0 | Comparative Example |
| 24 | | | | | | | | Treated | 4 | Example of the present invention |

*B: SUS304
**a: pulsed
***Oxalic acid-aqueous hydrogen peroxide-water (liquid temperature; 30° C.)

It is found that all our Examples exhibit the rating of 4 (antimicrobial activity value) so that they each keep excellent antimicrobial activity. With regard to the Comparative Examples in which no iodine-impregnation treatment is performed, the antimicrobial activity value is 0, that is, these Comparative Examples do not exhibit any antimicrobial activity.

Example 3

A Co—Cr alloy (mass % basis, 63.0% Co-6.0% Mo-2.0% Ni-0.25% C-rest Cr) was used as a base material to manuthe surface of the test piece with the iodine compound. In the iodine-impregnation treatment, the initial current density was about 0.2 A/dm².

With regard to the test pieces which were only anodically oxidized and test pieces subjected to iodine-impregnation treatment after anodically oxidized, an antimicrobial activity test was made by the film covering method according to the provisions of JIS Z 2801 to evaluate the antimicrobial activity of each test piece in the same manner as in Example 2. The method of evaluation was the same as that of Example 2.

The results obtained are shown in Table 4.

TABLE 4

| Test piece No. | Base material* | Anodic oxidation treatment Current load Type** | Anodic oxidation treatment Current load Frequency Hz | Film Presence or absence of micro pores or micro unevenesses | Film Number of micro pores (number/mm²) | Film thickness (μm) | Iodine-impregnation treatment Treated or untreated | Evaluation of antimicrobial activity Cells number after holding for 24 hr | Remarks |
|---|---|---|---|---|---|---|---|---|---|
| 31 | C | a | 3000 | Present | 7.6 × 10⁴ | 3.6 | Untreated | 0 | Comparative Example |
| 32 | | | | | | | Treated | 4 | Example of the present invention |

*C: Co—Cr alloy
**a: pulsed

It is found that all our Examples exhibit the rating 4 as the antimicrobial activity value so that they each keep excellent antimicrobial activity. With regard to the Comparative Examples in which no iodine-impregnation treatment is performed, the antimicrobial activity value is 0, that is, these Comparative Examples do not exhibit any antimicrobial activity.

Example 4

Stainless steel (SUS 304) was used as a base material to manufacture disc-test pieces for antimicrobial test (plate thickness: 2 mm). These test pieces were first subjected to shot blasting as mechanical processing treatment of mechanical treatment. The shot blasting was performed using four types of alumina shots one by one. In treatment in a first stage, a #60-mesh alumina shot was used to perform shot blasting under a pressure of 3.5 kg/cm² for about 2 minutes carefully from all directions so as not to leave non-blasted part. Then, in a second stage, the surface treated by shot blasting using #60 mesh shot was carefully shot-blasted using a #100-mesh alumina shot in the same pressure and time condition as in the first stage in such a manner as to be equally shot-blasted. Then, in a third stage, the surface treated by shot blasting using #100 mesh shot was carefully shot-blasted using a #150-mesh alumina shot in the same pressure and time condition as in the first and second stage in such a manner as to be equally shot-blasted. Then, in a fourth stage, the surface treated by shot blasting using #150-mesh shot was shot-blasted using a #200-mesh alumina shot in the same pressure and time condition as above. Accordingly, macro unevenness was provided to the surface of the test piece. The surface roughness in the shot-blasted state when measured according to the provisions of JIS B 0601-1994 was as follows: arithmetic average roughness Ra was 2 μm, maximum height of roughness profile Ry was 55 μm and ten-point height Rz of roughness profile was 3.5 μm.

Then, the test piece having the surface properties mentioned above was further subjected to medicinal treatment which was chemical treatment. In this medicinal treatment, the above test piece was treated by dipping the test piece in a mixture bath containing sulfuric acid (50 g)-oxalic acid (50 g)-water (400 g) at a liquid temperature of 60° C. for one hour. The shot-blasted surface was chemically oxidized into a micronized etching surface having an oxide film on the surface thereof. The surface roughness at this time was as follows: arithmetic average roughness Ra was 2.5 μm, maximum height of roughness profile Ry was 65 μm and ten-point height Rz of roughness profile was 4.3 μm.

The obtained test pieces were subjected to a scanning electron microscope (magnification: 2500 times) to observe the surface structure of the film (oxide film) formed on the surface of each test piece, thereby observing the number of micro unevennesses of the film formed on the surface of each test piece in the same manner as in Example 2.

Then, a part of the test pieces subjected to these treatments were thoroughly cleaned with water. Then, the test piece was dipped in an aqueous iodine compound solution (liquid temperature: 25° C.) prepared by dissolving 0.5 mass % of β-Cyclodextrin iodine (BCDI) which was an iodine compound in pure water and the test piece was settled on the anode side and a pure Ti plate was settled on the cathode side to perform electrolysis at a constant voltage of 150 V (direct current (DC)) for 3 minutes to cause electrophoresis, thereby carrying out iodine-impregnation treatment to electro-deposit the iodine compound on the micro unevennesses of the oxide film formed on the surface of the test piece. In the iodine-impregnation treatment, the initial current density was about 12 A/dm² and the current density was decreased gradually with passage of time.

With regard to the test pieces which were only mechanically treated and treated using a medicine and test pieces subjected to iodine-impregnation treatment after mechanically treated and treated using a medicine, an antimicrobial activity test was made by the film covering method according to the provisions of JIS Z 2801 to evaluate the antimicrobial activity of each test piece in the same manner as in Example 2. The cell numbers at the start of the test were 56000/ml (5.6×10⁴/ml). The method of evaluation was the same as that of Example 2.

The results obtained are shown in Table 5.

TABLE 5

| Test piece No. | Base material* | Mechanical processing treatment Type** | Medicine treatment Type*** | Film Presence or absence of micro pores or micro unevenesses | Film Number of micro pores (number/mm²) | Iodine-impregnation treatment Treated or untreated | Evaluation of antimicrobial activity Cells number after holding for 24 hr | Remarks |
|---|---|---|---|---|---|---|---|---|
| 41 | B | a | α | Present | 9.2 × 10⁴ | Untreated | 0 | Comparative Example |

TABLE 5-continued

| Test piece No. | Base material* | Mechanical processing treatment Type** | Medicine treatment Type*** | Film Presence or absence of micro pores or micro unevennesses | Film Number of micro pores (number/mm²) | Iodine-impregnation treatment Treated or untreated | Evaluation of antimicrobial activity Cells number after holding for 24 hr | Remarks |
|---|---|---|---|---|---|---|---|---|
| 42 | B | a | α | Present | $9.5 \times 10^4$ | Treated | 4 | Example of the present invention |

*B: SUS304
**a: shot blasting using an alumina shot
***α: dipping in 60° C. sulfuric acid-oxalic acid-water mixture solution It is found that all our Examples exhibit the rating of 4 as the antimicrobial activity value so that they each keep excellent antimicrobial activity. With regard to the Comparative Examples in which no iodine-impregnation treatment is performed, the antimicrobial activity value is 0, that is, these Comparative Examples do not exhibit any antimicrobial activity.

The invention claimed is:

1. A method of producing metallic medical supplies comprising:
supplying a metallic material selected from the group consisting of Ti, a Ti alloy, stainless steel and a Co—Cr alloy as a base material;
treating the base material by carrying out anodic oxidation treatment in which an acid electrolytic bath or an alkali electrolytic bath is used as an electrolytic solution, and pulsed current having a frequency of 50 to 10,000 Hz is applied to the base material in the electrolytic solution to carry out electrolysis treatment to form a film having micro pores and/or micro unevennesses having a density of $5 \times 10^4/mm^2$ or more on a surface of the base material; and
carrying out iodine-impregnation treatment to impregnate the film with iodine or iodine compounds,
wherein the metallic medical supplies have an antimicrobial activity value of not less than 2 to not more than 4.

2. The method according to claim 1, wherein the metallic medical supplies are subjected to a further medicinal treatment in which as alkali bath or acid bath having a liquid temperature of 30° C. or more is used and the base material is dipped in the alkali bath or acid bath.

3. The method according to claim 1, wherein the metallic medical supplies are subjected to a further shot blasting process.

4. The method according to claim 1, wherein the iodine compound is polyvinyl pyrrolidone iodine, β-cyclodextrin iodine or silver iodide.

5. The method of producing metallic medical supplies according to claim 1, wherein the electrolysis treatment includes applying a voltage of 100 V or higher to the base material.

6. The method of producing metallic medical supplies according to claim 1, wherein the electrolysis treatment includes applying a voltage of 150 V or higher to the base material.

7. The method of producing metallic medical supplies according to claim 1, wherein the base material is made of Ti or a Ti alloy.

8. The method of producing metallic medical supplies according to claim 7, wherein the electrolysis treatment includes applying a voltage of 100 V or higher to the base material.

9. The method of producing metallic medical supplies according to claim 7, wherein the electrolysis treatment includes applying a voltage of 150 V or higher to the base material.

10. The method of producing metallic medical supplies according to claim 7, wherein the iodine compound is polyvinyl pyrrolidone iodine, b-cyclodextrin iodine or silver iodine.

11. The method of producing metallic medical supplies according to claim 7, wherein the iodine compound is polyvinyl pyrrolidone iodine.

12. The method of producing metallic medical supplies according to claim 1, wherein the iodine-impregnation treatment for impregnation with iodine or iodine compound is an electrolytic treatment in which the base material is dipped in an aqueous iodine or iodine compound solution, and direct current is applied by using the base material as an anode to carry out electrolysis at a constant voltage or constant current density.

13. The method of producing metallic medical supplies according to claim 12, wherein the constant voltage is a constant voltage ranging from 100 to 200 V.

14. The method of producing metallic medical supplies according to claim 13, wherein the constant voltage is applied for 1 to 10 minutes.

15. The method of producing metallic medical supplies according to claim 12, wherein the constant current density is a constant current density ranging from 0.05 to 10 A/dm².

16. The method of producing metallic medical supplies according to claim 12, wherein the iodine compound is polyvinyl pyrrolidone iodine, b-cyclodextrin iodine or silver iodine.

17. The method of producing metallic medical supplies according to claim 12, wherein the iodine compound is polyvinyl pyrrolidone iodine.

18. A method of retaining antimicrobial activity on metallic medical supplies comprising:
conducting an anodic oxidation treatment on a surface of a base material of the metallic medical supplies including the base material made of a metal selected from the group consisting of Ti, a Ti alloy, stainless steel and a Co—Cr alloy to obtain a film having micro pores in a density of at least $5 \times 10^4/mm^2$; and
impregnating the micro pores with iodine or iodine compounds,
wherein the metallic medical supplies have an antimicrobial activity value of not less than 2 to not more than 4.

* * * * *